US007536226B2

(12) United States Patent
Williams et al.

(10) Patent No.: US 7,536,226 B2
(45) Date of Patent: May 19, 2009

(54) ELECTRO-NERVE STIMULATOR SYSTEM AND METHODS

(75) Inventors: Jeffrey M. Williams, Andover, MN (US); Fred Van Aart, Lage Zwaluwe (NL); Hans Van Den Biggelaar, Haaren (NL); Plet Van Helvoirt, Boekel (NL); Petronella Maria Coleta van Laanen, legal representative, Boekel (NL)

(73) Assignee: Uroplasty, Inc., Minnetonka, MN (US)

( * ) Notice: Subject to any disclaimer, the term of this patent is extended or adjusted under 35 U.S.C. 154(b) by 496 days.

(21) Appl. No.: 10/492,578

(22) PCT Filed: Oct. 18, 2002

(86) PCT No.: PCT/US02/33318

§ 371 (c)(1),
(2), (4) Date: Sep. 13, 2004

(87) PCT Pub. No.: WO03/033068

PCT Pub. Date: Apr. 24, 2003

(65) Prior Publication Data

US 2005/0171576 A1     Aug. 4, 2005

Related U.S. Application Data

(60) Provisional application No. 60/336,074, filed on Oct. 18, 2001.

(51) Int. Cl.
*A61N 1/00*      (2006.01)
(52) U.S. Cl. ...................................... 607/115
(58) Field of Classification Search ......... 607/115–116, 607/149; 606/129; 600/372, 377, 382, 386–392
See application file for complete search history.

(56) References Cited

U.S. PATENT DOCUMENTS 3,893,462 A     7/1975   Manning ............... 128/421

(Continued)

FOREIGN PATENT DOCUMENTS

GB          2 336 214       10/1999

(Continued)

OTHER PUBLICATIONS

SANS Examine the revolutionary SANS™ device at EAU Stand 9.05., UroSurge (1998).

(Continued)

*Primary Examiner*—Angela D Sykes
*Assistant Examiner*—Rex Holmes
(74) *Attorney, Agent, or Firm*—Cyr & Associates, P.A.

(57) ABSTRACT

An electro-nerve stimulation apparatus includes a pulse generator, a first electrically conductive, insulated lead wire, a second electrically conductive, insulated lead wire, an electrically conductive transcutaneous electrode and an electrically conductive percutaneous needle electrode. Connected to one end of the first and second lead wires is a connector for electrically coupling with the pulse generator. The transcutaneous electrode is operably connected to the other end of the first lead wire. An electrically conductive adaptor is secured to the other end of the second lead wire for electrically coupling to the terminal end of the percutaneous needle electrode. The lead wire set includes a single-use mechanism adapted to effectively discourage reuse of the electrodes. In use, the transcutaneous electrode is adhered to the patient's skin distal from the desired internal stimulation site. The percutaneous needle electrode is inserted through the skin in proximity to the desired internal stimulation site. The pulse generator is activated to pass current pulses between the transcutaneous electrode and the percutaneous needle electrode through the internal stimulation site.

32 Claims, 4 Drawing Sheets

U.S. PATENT DOCUMENTS

| | | | | |
|---|---|---|---|---|
| 3,995,644 | A | | 12/1976 | Parsons ................... 128/418 |
| 4,406,288 | A | | 9/1983 | Horwinski et al. .......... 128/422 |
| 4,408,609 | A | * | 10/1983 | Axelgaard ................. 607/43 |
| 4,519,394 | A | | 5/1985 | Black et al. ............... 128/419 |
| 4,535,785 | A | | 8/1985 | van den Honert et al. ... 128/746 |
| 5,056,518 | A | | 10/1991 | Pethica et al. ............. 128/419 |
| 5,094,242 | A | | 3/1992 | Gleason et al. ............ 128/642 |
| 5,562,710 | A | | 10/1996 | Olsen et al. ................ 607/5 |
| 5,679,022 | A | | 10/1997 | Cappa et al. ............... 439/502 |
| 5,695,495 | A | | 12/1997 | Ellman et al. .............. 606/41 |
| 5,782,892 | A | | 7/1998 | Castle et al. ............... 607/37 |
| 5,857,968 | A | | 1/1999 | Benja-Athon .............. 600/372 |
| 5,906,634 | A | | 5/1999 | Flynn et al. ............... 607/37 |
| 5,951,484 | A | | 9/1999 | Hoium et al. |
| 5,954,758 | A | | 9/1999 | Peckham et al. ........... 607/48 |
| 6,141,585 | A | | 10/2000 | Prutchi et al. ............. 607/8 |
| 6,233,482 | B1 | | 5/2001 | Hofmann et al. ........... 604/21 |
| 6,493,588 | B1 | | 12/2002 | Malaney et al. ............ 607/46 |
| 6,516,227 | B1 | * | 2/2003 | Meadows et al. ........... 607/46 |
| 6,904,324 | B2 | * | 6/2005 | Bishay ..................... 607/149 |
| 2002/0055762 | A1 | * | 5/2002 | Gliner ..................... 607/46 |

FOREIGN PATENT DOCUMENTS

| | | |
|---|---|---|
| WO | WO 97/49453 | 12/1997 |
| WO | WO 99/47204 | 9/1999 |

OTHER PUBLICATIONS

SANS "Introducing an innovative point of treatment for urge incontinence," UroSurge (1998).

SANS "Introducing two New Treatments for Stress and Urge Incontinence," UroSurge (1998).

SANS "Bold innovations in urology. Visit UroSurge at the EAU Convention.," UroSurge (1998).

"Sacral Nerve Stimulation Improves Chronic Voiding Dysfunction Symptoms," Medtronic (undated).

Stoller, M.L., "Needle Stimulation (through the skin) for the Treatment of Incontinence," Quality Care, vol. 16, No. 1 (Winter 1998), pp. 1-2 (mailed Feb. 1998).

Stoller, M.L. et al, "The Efficacy of Acupuncture in Reversing the Unstable Bladder in Pig-Tailed Monkeys," O AM Urological, (1998).

Bolz, A., "Die Bedeutung Der Phasengrenze Zwischen Alloplastischen Festkorpern Und Biologischen Geweben Fur Die Elektrostimulation," pp. 11-15 (Feb. 1995).

Urbasvek, A., "Konzeption Und Technische Losungen Zur Optimierung Der Frequenzadaptiven Elektrostimulation Des Herzens," pp. 23-25 (May 1995).

Interstitial Cystitis Network, "Urosurge's PercSANS receives FDA approval for frequency, urgency & more," Interstitial Cystitis Newsletter, Feb. 10, 2000, 6 pages.

Japan External Trade Organization, "Health Care '97 brings Midwest firms face-to-face with success," JETRO Midwest Newsletter, Jul./Aug. 1997, 4 pages.

Stoller, Marshall, "SANS—Stroller afferent nerve stimulation for frequency, urgency and incontinence," Interstitial Cystitis Network—Chat Log (www.ic-network.com), Mar. 7, 2000, 6 pages.

University of Iowa, "New treatment for urinary incontinence at UI receives FDA approval," University of Iowa Health Care News, Feb. 28, 2000, 2 pages.

* cited by examiner

ELECTRO-NERVE STIMULATOR SYSTEM AND METHODS

BACKGROUND OF THE INVENTION

1. Field of the Invention

The present invention relates generally to electro-nerve stimulation and more particularly to electro-nerve stimulation systems utilizing transcutaneous and percutaneous electrodes.

2. Description of the Related Art

An electro-nerve stimulation system is disclosed in U.S. patent application Ser. No. 09/213,558 comprising a pulse generator electrically coupled by lead wires to an electrically conductive transcutaneous electrode (i.e., an electrode which does not penetrate the surface of the skin) and an electrically conductive percutaneous needle electrode (i.e., an electrode which penetrates the surface of the skin). In use, the transcutaneous electrode is positioned distally proximate the stimulation site. The percutaneous electrode needle, is positioned to penetrate the patient's skin and is advanced into proximity with the stimulation site. In this configuration, electrical current pulses from the pulse generator traverse the internal stimulation site by passing from the transcutaneous electrode to the percutaneous needle. This type of electro-nerve stimulation system disclosed in the '558 application has been found to be effective for both nerve and muscle stimulation for treatment of numerous conditions, including urge incontinence, chronic pain, Parkinson's disease, multiple sclerosis and for general muscle and joint rehabilitation.

While the foregoing electro-nerve stimulation system as disclosed in the above referenced '558 application serves its intended purpose, non-medical professionals who use the system for self treatment and for treating others, may not readily appreciate the health risks associated with re-using the same electrodes that may have come in contact with another person's skin and bodily fluids. Accordingly, there is a need in the industry for an electro-nerve stimulation system which provides the features and advantages disclosed in the above referenced '558 application, but which is designed to effectively prevent the electrodes from being reused for a second treatment. To the accomplishment effectively preventing reuse of the electrodes, the retail cost of disposable electrodes and their associated lead wires must be relatively inexpensive so that any perceived benefit in attempting to reuse the disposable electrodes is outweighed by the difficulty in attempting to do so.

SUMMARY OF THE INVENTION

The present invention is an electro-nerve stimulation system comprising a pulse generator electrically coupled by first and second electrically conductive insulated lead wires to an electrically conductive transcutaneous electrode and an electrically conductive percutaneous needle electrode, respectively. One end of each of the first and second electrically conductive, insulated lead wires are preferably fixedly secured to a single male keyed connector which is matingly receivable by a single female keyed receptacle on the pulse generator. The other end of the first lead wire is fixedly secured to the electrically conductive transcutaneous electrode. One face of the transcutaneous electrode includes an electrically conductive medical grade adhesive to removably adhere the electrode to the patient's skin near the desired stimulation site. Fixedly secured to the other end of the second lead wire is an electrically conductive adaptor. In the preferred embodiment the electrically conductive adaptor is a tape member. The electrically conductive tape member preferably includes an electrically conductive adhesive portion and a non-adhesive portion. The percutaneous needle electrode is preferably fixedly securable to the tape member by folding the adhesive portion of the tape member over the end of the percutaneous needle extending from the patient's skin.

In use, the transcutaneous electrode with the first lead wire secured thereto is positioned and adhered to the patient's skin distally proximate the stimulation site. The percutaneous needle electrode, which is not yet electrically connected to the electrically conductive tape member, is positioned to penetrate the patient's skin and is advanced into proximity with the stimulation site. The first ends of the lead wires are electrically connected to the pulse generator by inserting the preferred single male connector into the mating female receptacle of the pulse generator. The pulse generator is activated. The end of the percutaneous needle electrode projecting outwardly from the patient's skin is placed and held in contact with the non-adhesive portion of the electrically conductive tape. The position of the percutaneous needle electrode is manipulated as needed until it is determined that the percutaneous needle is at the desired location in proximity to the desired stimulation site. Once it is determined that the percutaneous needle electrode is properly positioned, the needle is preferably fixedly secured to the electrically conductive tape by folding the ends of the adhesive portion of the electrically conductive tape member over the projecting end of the needle electrode thereby forming an electrical connection therebetween. In this configuration, current pulses generated by the pulse generator traverse the internal stimulation site from the transcutaneous needle electrode to the percutaneous needle electrode.

The adhesive on the face of the transcutaneous electrode for adhering to the patient's skin is preferably a single-use adhesive in that it will lose its adhesive properties upon removal such that it will not readily re-adhere to the patient's skin, thereby effectively rendering the transcutaneous electrode to a single use. The electrically conductive tape member is also preferably adapted for only a single use in that once the ends of the adhesive portion of the tape member is folder over the end of the percutaneous needle electrode, the folded ends of the tape member cannot be readily reopened for removal of the percutaneous needle adhered therein without damaging the tape member. In addition, or alteratively, the preferred single male connector is adapted for only a single use. In one alternative embodiment, the connector includes a fuse which will burn out after a preselected time period, thereby rendering the connector incapable of making an electrically conductive connection with the lead wire interfaces of pulse generator. Alternatively, after expiration of the preselected time period, the pulse generator may generate a current spike to burn out the fuse. In yet another alternative embodiment, a serial read/write non-volatile EPROM chip may be incorporated into the connector which is programmable to prevent an electrical connection with the lead wire interface of the pulse generator after a predetermined time period. In yet another alternative embodiment, the connector may incorporate both a serial read/write non-volatile EPROM and a fuse in which the EPROM is programmable to burn out the fuse after a preselected time period or to generate a spike to burn out the fuse after expiration of a preselected time period.

In still another alternative embodiment the adaptor secured to the second end of the second lead wire may be a clip for connecting with the terminal end of the percutaneous needle electrode. To prevent reuse of the needle electrode and the lead wire set, the clip is preferably designed to fail after one use. For example, the clip may have a bridge member movable between an open position and a closed position by depressing the plunger. As current pulses from the pulse generator traverse the bridge member, the bridge member may burn out preventing its reuse, or alternatively, the bridge member may fixedly bond or weld to the terminal end of the percutaneous needle electrode preventing reuse of the electrode and clip. In the alternative, or in addition thereto, this embodiment may also be used with one or more of the alternative single-use connector embodiments described above. If a single-use connector is used, the clip need not be a single-use clip.

To the accomplishment of the above objectives, features and advantages, this invention may be embodied in the forms illustrated in the accompanying drawings, attention being called to the fact, however, that the drawings are illustrative only, and that changes may be made in the specific form illustrated and described within the scope of the appended claims.

DETAILED DESCRIPTION OF THE INVENTION

Figure 1:
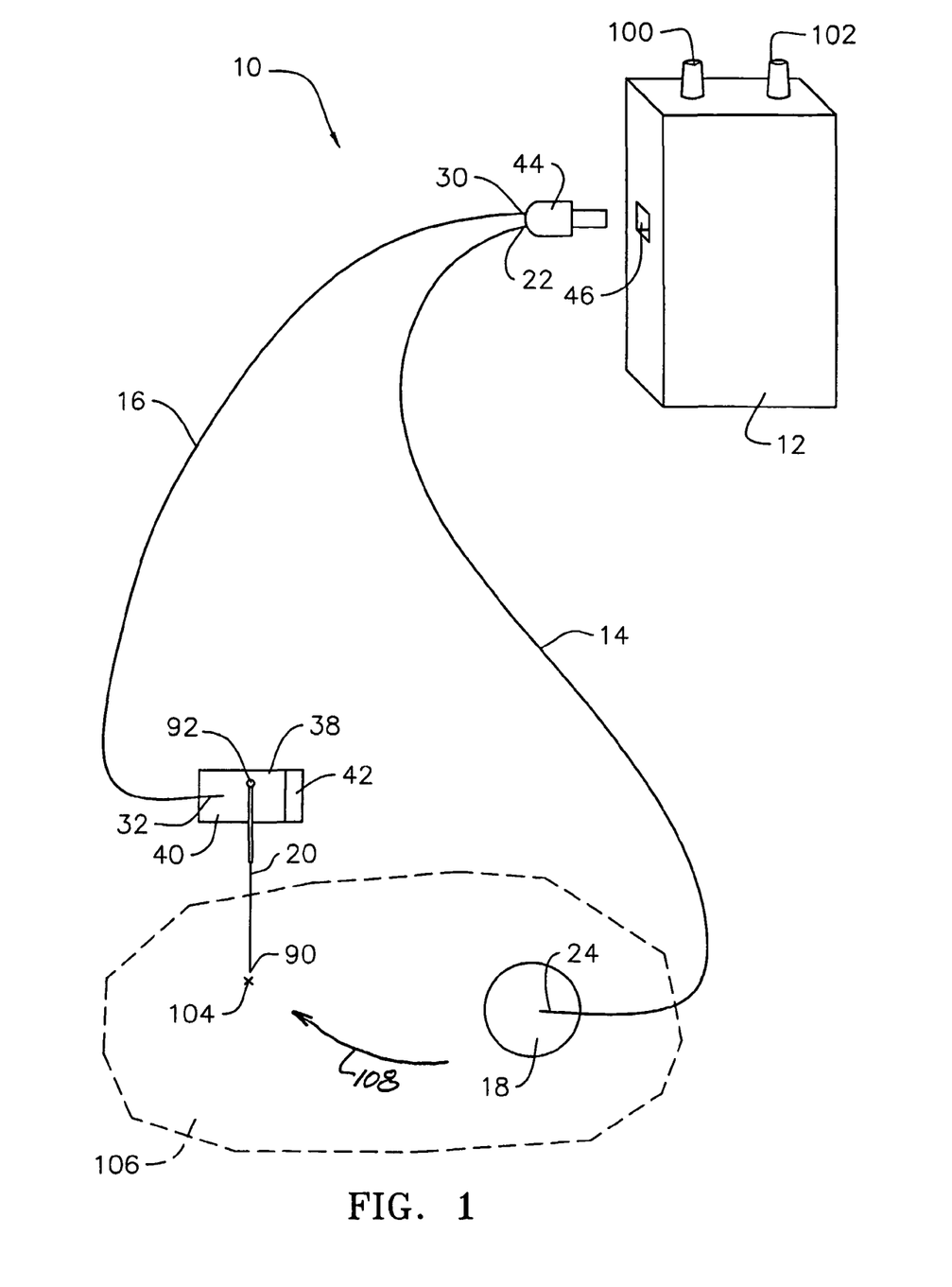
FIG. 1 illustrates the preferred embodiment of the electro-nerve stimulator system of the present invention.

The electro-nerve stimulation apparatus 10 of the present invention, as illustrated in FIG. 1, comprises a pulse generator 12, a first electrically conductive, insulated lead wire 14, a second electrically conductive, insulated lead wire 16, an electrically conductive transcutaneous electrode 18 and an electrically conductive percutaneous needle electrode 20.

In the preferred embodiment of the apparatus 10, the first lead wire 14 has a first end 22 and a second end 24. The first end 22 electrically couples to a first lead wire interface of the pulse generator 12. The transcutaneous electrode 18 is preferably fixedly secured to the second end 24 of the first lead wire 14 as described in detail later.

Figure 12:
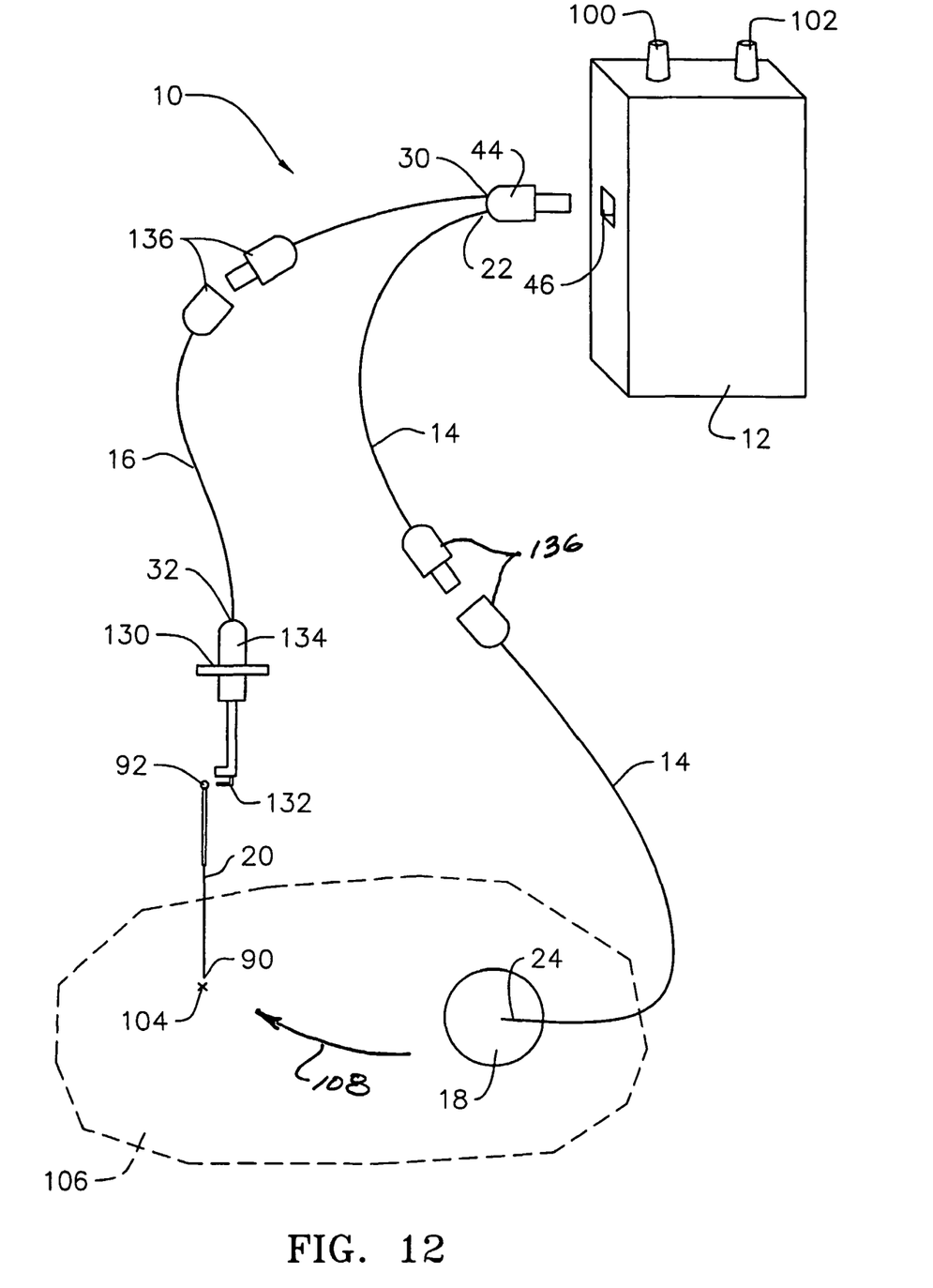
FIG. 12 illustrates another embodiment of the lead wire set for use with the present invention utilizing a clip for electrically coupling the lead wire to the percutaneous needle electrode.

The second lead wire 16 has a first end 30 and a second end 32. The first end 30 of the second lead wire 16 electrically couples to a second lead wire interface of the pulse generator 12. Fixedly secured to the second end 32 of the second lead wire is an electrically conductive adaptor. The adaptor is preferably an electrically conductive tape member 38 as shown in FIG. 1. In an alternative embodiment, the adaptor may be an electrically conductive clip 130 as illustrated in FIG. 12, for example.

The preferred electrically conductive tape member 38 includes an electrically conductive adhesive portion 40 and an electrically conductive non-adhesive portion 42 the purpose of which will be described in detail later.

In the preferred embodiment, the first ends 22, 30 of the first and second lead wires 14, 16 are fixedly secured to a single male connector 44 which is matingly receivable by a single mating female receptacle 46. The preferred single male connector 44 and single female receptacle 46 are also preferably keyed in any conventional manner to ensure that the first lead wire 14 will only electrically couple with the first lead wire interface and that the second lead wire 16 will only electrically couple with the second lead wire interface. This safeguard will ensure that the current pulses generated by the pulse generator 12 will flow from the transcutaneous electrode 18 to the percutaneous needle electrode 20 as describe in detail later.

Figure 2:
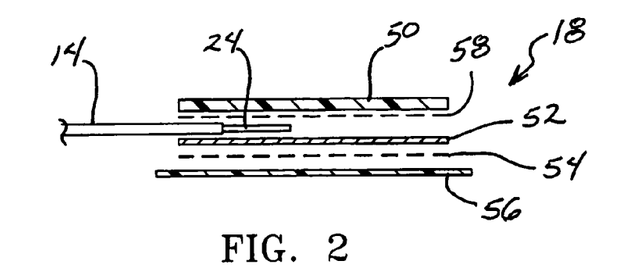
FIG. 2 is an exploded cross-sectional view of the preferred embodiment of the transcutaneous electrode of the present invention.

Referring now to FIG. 2, an exploded, cross-sectional view of the preferred transcutaneous electrode 18 is illustrated. The preferred transcutaneous electrode 18 includes various layers sandwiched together, including a non-electrically conductive top layer 50, an intermediate electrically conductive foil 52, such as aluminum foil, and a bottom electrically conductive adhesive layer 54, preferably biocompatible and hypoallergenic, for adhering to the transcutaneous electrode 18 to the patient's skin as described later. A removable backing strip 56 is preferably disposed over the lower face of the adhesive layer 54 which is then removed just prior to adhering the transcutaneous electrode 18 to the patient's skin. Disposed between the lower face of the top layer 50 and the upper face of the electrically conductive layer 52 is another adhesive layer 58 which bonds the top non-conductive layer 50 to the intermediate conductive layer 54. The second end 24 of the first lead wire 14 is disposed between the top non-conductive layer 50 and the intermediate conductive layer 52. A portion of the insulation is removed from the first lead wire 14 such that an electrical connection may be created with the electrically conductive layer 52. The adhesive 58 preferably securely bonds the second end 24 of the first lead wire 14 to the conductive layer 52 to such that it cannot be readily removed therefrom without damaging the electrode 18. In the preferred embodiment, the adhesive comprising the bottom adhesive layer 54 is preferably a single-use adhesive, meaning that the adhesive loses its adhesive properties upon its removal and will not readily re-adhere to the patient's skin, such that the transcutaneous electrode 18 is essentially non-reusable after one use.

Figure 3:
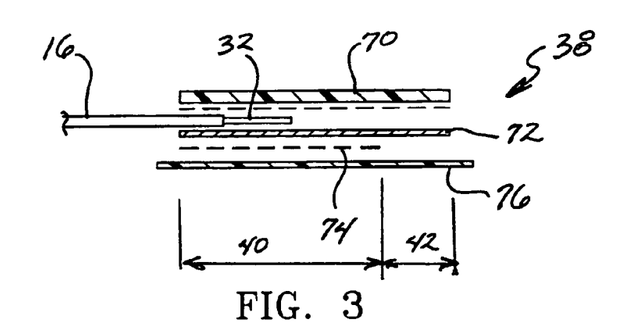
FIG. 3 is an exploded cross-sectional view of the preferred embodiment of the electrically conductive tape member of the present invention.

Referring now to FIG. 3, an exploded, cross-sectional view of the preferred electrically conductive tape member 38 is illustrated. The tape member 38 also preferably includes various layers sandwiched together, including a non-electrically conductive top layer 70, an intermediate electrically conductive foil layer 72, such as aluminum foil, and a bottom electrically conductive adhesive layer 74 preferably extending over only a portion of the tape member 38 (see also FIG. 4). The remaining portion of the tape member 38 preferably does not include any adhesive. A removable backing strip 76 is preferably disposed over the lower face of the bottom adhesive layer 74 which is then removed just prior to adhering the percutaneous needle electrode 20 thereto (discussed later). Disposed between the lower face of the top layer 70 and the upper face of the electrically conductive layer 72 is another adhesive layer 78 which bonds the top non-conductive layer 70 to the intermediate conductive layer 74. The second end 32 of the second lead wire 16 is disposed between the top non-conductive layer 70 and the intermediate conductive layer 72. A portion of the insulation is removed from the second lead wire 16 such that an electrical connection may be created with the electrically conductive layer 72. The adhesive 78 preferably securely bonds the second end 32 of the second lead wire 16 to the conductive layer 72 to such that it cannot be readily removed therefrom without damaging the tape member 38. In the preferred embodiment, the tape member 38 is preferably adapted for only a single-use whereby the adhesive comprising the bottom adhesive layer 74 has sufficiently adhesive properties such that when the opposing ends of the tape member 38 are folded over onto each other and over the terminal end 92 of percutaneous needle electrode 20 (as discussed later) the ends of the tape member 38 cannot be readily unfolded thereby fixedly securing the percutaneous needle electrode 20 therebetween.

The percutaneous needle electrode 20 (FIG. 1) is preferably constructed out of medical grade stainless steel or other biocompatible electrically conductive metal. The includes a first end 90 for insertion into the patient's body in proximity to the preselected internal stimulation site (discussed later) and a second end 92 to which the tape member 38 is to be electrically coupled. The size of the needle electrode 20 is preferably small, for example 34G needle electrode (0.22×10 mm), to minimize trauma during insertion. The second end 92 of the needle electrode 20 preferably includes an enlarged portion to enable the electrically conductive tape member 38 to be more easily adhered thereto (discussed later).

Referring again to FIG. 1, the pulse generator 12 is preferably a small hand-held, battery operated pulse generator that produces small electrical current pulses, preferably between 1-10 mA, which pass between the transcutaneous electrode 18 and the percutaneous needle electrode 20. The pulse generator 12 may be of the type disclosed in U.S. patent application Ser. No. 09/213,558, which is incorporated herein by reference. A commercially available current pulse generator manufactured by Finetech-Medical for the treatment of dropped foot has also been determined to be suitable for the present invention with minor modification to achieve the functionality and desired features of the present invention. Those skilled in the art would readily appreciate how to make such modifications of the Finetech-Medical pulse generator and therefore further discussion as to these modifications is not warranted. The preferred pulse generator 12 includes a first dial 100 used for selecting the desired current pulse for treatment, preferably in increments of 1 mA. The preferred pulse generator 12 further includes a second dial 102 for setting the desired treatment time preferably in five minute increments. The pulse generator 12 preferably generates an audible and/or visible signals. For example, a audible and/or visible signal may be initially generated when the pulse generator is turned on and when the dial 102 is turned past each of the predefined time increments. Additionally, an audible and/or visual signal may be generated, for example, when one half of the remaining time selected for the treatment has expired. Also, when the time selected for the treatment expires, another audible and/or visual signal may be generated.

Figure 4:
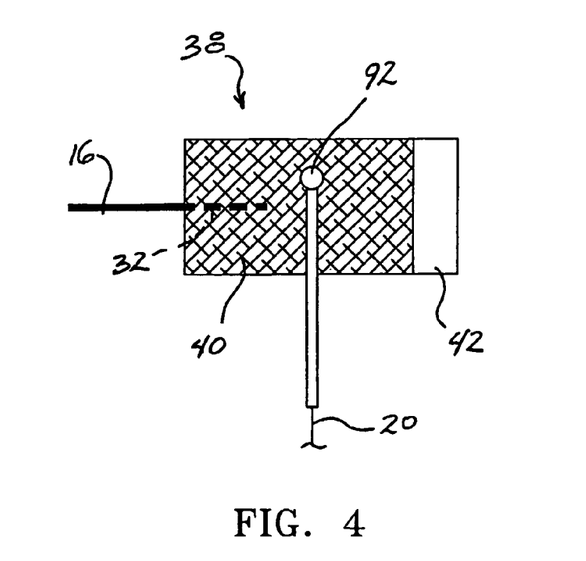
FIG. 4 illustrates the positioning of the terminal end of the percutaneous needle electrode onto the adhesive portion of the electrically conductive tape member of the present invention.
Figure 5:
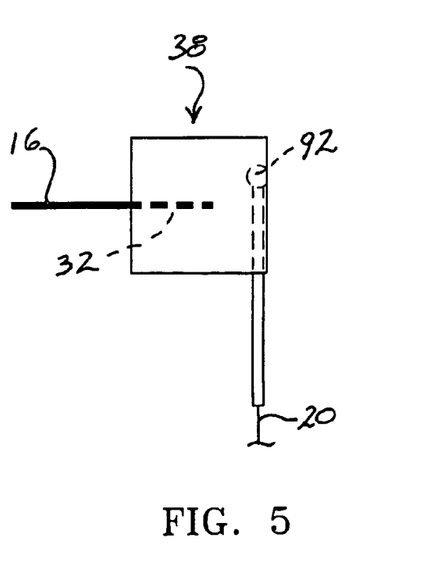
FIG. 5 illustrates the electrically conductive tape member of the present invention fixedly adhered to the terminal end of the percutaneous needle electrode.

As illustrated in FIG. 1, in use, the desired internal stimulation site 104 on the patient's body 106 is determined depending on the treatment for which the electro-nerve stimulation system is to be used. The first end 90 of the percutaneous needle electrode 18 is positioned to penetrate the patient's skin and is advanced into proximity with the preselected internal stimulation site. The adhesive backing 56 on the transcutaneous electrode 18 is removed and the adhesive face 54 of the transcutaneous electrode 18 is pressed onto the surface of the patient's skin at the desired location, preferably distally (i.e., downstream) of the internal stimulation site. The adhesive backing 76 on the electrically conductive tape member 38 is removed and the terminal end of the percutaneous needle electrode 20 (i.e. the end extending from the patient's body) is positioned at approximately the midpoint of the tape member 38 as illustrated in FIG. 4. The percutaneous needle electrode 20 is then preferably fixedly adhered to the tape member as shown in FIG. 5 by folding the ends of the tape member 38 over the terminal end 92 of the needle electrode 20. The first and second lead wires 14, 16 are then electrically coupled to the pulse generator 12 by inserting the male connector 44 into the mating female receptacle 46. The pulse generator 12 is activated to generate current pulses. The current pulses from the pulse generator 12 traverse the internal stimulation site 104 by passing from the transcutaneous electrode 18 to the percutaneous needle electrode 20 as indicated by the arrow 108.

It may be desirable to test whether the percutaneous needle electrode 20 is properly positioned in proximity to the internal stimulation site 104 prior to fixedly adhering the electrode 20 to the tape member 38. Accordingly, in the preferred embodiment the electrically conductive tape member 38 includes a non-adhesive portion 42. By holding the needle electrode 20 against the non-adhesive portion 42 of the electrically conductive tape member 38 while the pulse generator is activated, the user will be able to test whether the needle electrode 20 is properly positioned in proximity to the preselected internal stimulation site 104 to achieve the desired treatment results. If the needle electrode 20 is not properly positioned, the tape member 38 can simply be removed and the electrode needle repositioned or manipulated into the proper position.

Figure 6:
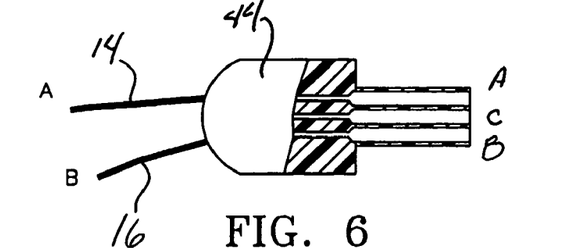
FIG. 6 is a partial cross-sectional view of the preferred embodiment of single-use connector for an embodiment of the present invention.
Figure 7:
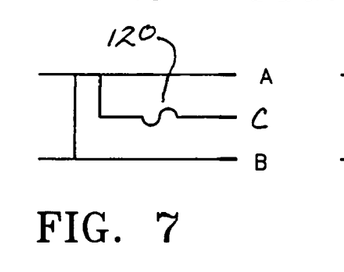
FIG. 7 is an electrical schematic for one embodiment of the single-use connector of FIG. 6.
Figure 8:
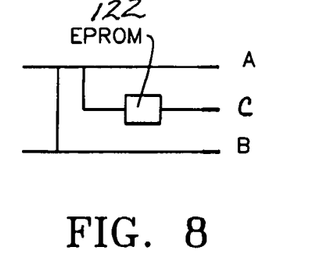
FIG. 8 is an electrical schematic for another embodiment of the single-use connector of FIG. 6.
Figure 9:
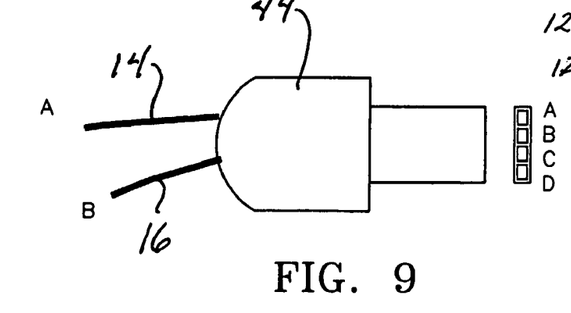
FIG. 9 illustrates another embodiment of a single use connector for an embodiment of the present invention.

In order to further ensure that the electrodes 18, 20 and associated lead wires 14, 16 are not readily re-usable after coming into contact with a patient's skin or bodily fluids, the connector 44 may also be adapted to fail after a single use or after a predetermined time period. FIGS. 6-8 illustrate possible embodiments for the connector 44 adapted for a single use. The connector 44 may include two ports A and B corresponding to the first and second lead wires 14, 16 (also designated by corresponding reference letters A and B). A third port C may include a fuse 120 which may be adapted to burn out after a preselected time period, thereby rendering the connector 44 incapable of making an electrical connection between the first and second lead wires 14, 16 with the lead wire interfaces of the pulse generator 12. Alternatively, as illustrated in FIG. 8, the connector 44 may include a serial read/write non-volatile erasable, programmable read only memory (EPROM) chip 122 programmable to prevent the lead wires 14, 16 from making an electrical connection with the lead wire interfaces of the pulse generator 12 after a predetermined time period. In yet another embodiment, as shown in FIGS. 9-10, the connector 44 may incorporate both a serial read/write non-volatile EPROM 122 and a fuse 120 in which the EPROM 122 is programmable to burn out the fuse after a preselected time period or to generate a current spike to burn out the fuse after expiration of a preselected time period.

Figure 10:
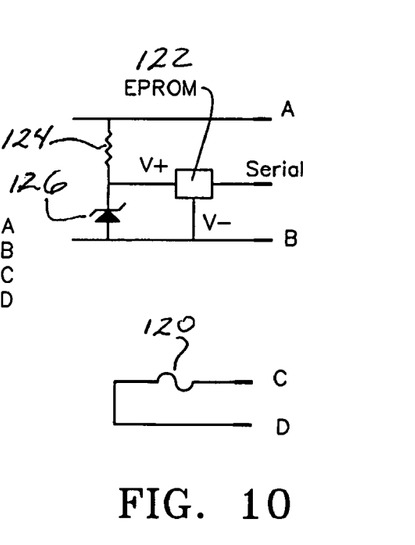
FIG. 10 is an electrical schematic for one embodiment of the single-use connector of FIG. 9.
Figure 11:
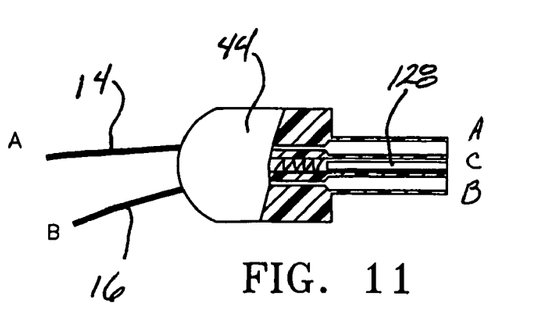
FIG. 11 illustrates another embodiment of a mechanical single use connector for an embodiment of the present invention.

An illustrative electrical schematic is shown in FIG. 10 for this embodiment which may include a resister 124 and a zenor diode 126. In yet another alternative embodiment as shown in FIG. 11, a mechanical mechanism may be employed in which a pin 128 is biased within port C. In operation, upon insertion of the connector 44 into the female receptacle 46 of the pulse generator 12 the mechanism is actuated to release the biased pin 128. Upon removal of the connector 44 from the female receptacle 46, the released pin 128 prevents the connector from being reinserted into the female receptacle 46 thereby preventing the first and second lead wires 14, 16 from electrically coupling with the first and second lead wire interfaces of the pulse generator 12.

In still another alternative embodiment as illustrated in FIG. 12, the electrically conductive adaptor may comprise a clip 130 for connecting with the terminal end 92 of the percutaneous needle electrode 20. The clip 130 may have a bridge member 132 movable between an open position and a closed position by depressing the plunger 134. As current pulses from the pulse generator 12 traverse the bridge member 132, the bridge member may burn out preventing its reuse, or alternatively, the bridge member may fixedly bond or weld to the terminal end 92 of the percutaneous needle electrode 20 preventing reuse of the electrode and clip 130. This embodiment may also be used with one or more of the alternative connector 44 embodiments described above. If a single-use connector 44 as identified above is used with the clip 130, the clip need not be a single-use clip 130 as just described. Also as shown in FIG. 12, the first and second lead wires 14 may include intermediate lead wire connectors 136 so the entire lead wire set does not need replacing.

Naturally, it is not possible to design a system which is completely capable of preventing a determined individual from refurbishing the lead wires and/or electrodes so that they may be reused. Thus, reference to single-use adhesives, single-use connectors, or single-use adaptors as used herein does not mean that these devices must be completely incapable of reuse. Rather as used herein, the term "single-use" should be understood as meaning that the disclosed structure, or its equivalent, for performing the intended function is sufficiently degraded or destroyed so that the structure does not perform its intended function as efficiently or that the structure is sufficiently degraded or destroyed to discourage or at least make it difficult to re-use the structure for its intended function.

The apparatus and system 10 of the present invention is particularly suited for the treatment of urinary urge incontinence. The percutaneous needle electrode 20 is inserted into the patient's skin in proximity to the tibial nerve cephalic to the medial malleolus. The transcutaneous electrode is adhered to the patient's skin distal to the percutaneous needle electrode. Those skilled in the art will appreciate that the nerve stimulation system of the present invention is effective not only for the treatment of urge incontinence, but can also be effective for both nerve and muscle stimulation to treat numerous other conditions including gastro-reflux, chronic pain, Parkinson's disease, multiple sclerosis and general joint and muscle rehabilitation.

Although only certain exemplary embodiments of the invention have been described in detail above, those skilled in the art will readily appreciate that many modifications are possible without materially departing from the novel teachings and advantages of this invention. Accordingly, all such modifications are intended to be included within the scope of this invention as defined in the following claims.

The invention claimed is:
1. An electro-nerve stimulation apparatus, comprising:
a pulse generator for generating electrical pulses, said pulse generator having a first lead wire interface and a second lead wire interface;
a percutaneous needle electrode; and
a lead wire set removably connectable to the pulse generator and comprising;
a first electrically conductive, insulated lead wire having first and second ends, said first end of said first lead wire comprising a first connector for electrically coupling with said first lead wire interface of said pulse generator, said second end of said first lead wire operably comprising an electrically conductive transcutaneous electrode for delivering electrical pulses generated by the pulse generator to a patient's skin;
a second electrically conductive, insulated lead wire having first and second ends, said first end of said second lead wire comprising a second connector for electrically coupling with said second lead wire interface of said pulse generator, said second end of said second lead wire comprising an electrically conductive and mechanically suspendable attachment member for being suspended by and electrically connecting with said percutaneous needle electrode; and
a single-use mechanism comprising a part of said lead wire set to effectively discourage re-use thereof;
wherein said attachment member includes an electrically conductive tape member having an adhesive portion;
wherein a terminal end of said percutaneous needle electrode is fixedly adhered to said adhesive portion of said electrically conductive tape member, whereby said percutaneous needle electrode is not readily removable therefrom without damaging said tape member; and
wherein said electrically conductive tape member further includes a non-adhesive electrically conductive portion for testing proper placement of said other end of said percutaneous needle electrode in proximity to said internal stimulation site prior to adhering said terminal end of said percutaneous needle electrode to said adhesive portion of said electrically conductive tape member.

2. The apparatus of claim 1, wherein said electrically conductive transcutaneous electrode includes adhesive on a face thereof for removably securing said transcutaneous electrode onto said patient's body at a desired location.

3. The apparatus of claim 2, wherein said adhesive on said face of said transcutaneous electrode is a single-use adhesive such that upon removal of said transcutaneous electrode from said patient's skin said adhesive will not readily readhere to said patient's skin.

4. An electro-nerve stimulation apparatus, comprising:
a pulse generator for generating electrical pulses, said pulse generator having a first lead wire interface and a second lead wire interface;
a first electrically conductive, insulated lead wire having first and second ends, said first end of said first lead wire fixedly secured to a first connector for electrically coupling with said first lead wire interface of said pulse generator, said second end of said first lead wire operably secured to an electrically conductive transcutaneous electrode for delivering electrical pulses generated by the pulse generator to a patient's skin;
a second electrically conductive, insulated lead wire having first and second ends, said first end of said second lead wire fixedly secured to a second connector for electrically coupling with said second lead wire interface of said pulse generator, said second end of said second lead wire fixedly secured to an electrically conductive adaptor for electrically connecting with a terminal end of a percutaneous needle electrode; and a single male connector comprising said first and second connectors fixedly secured to said first ends of said first and second lead wires;

wherein said pulse generator includes a single mating female receptacle for electrically coupling said first and second lead wires with said first and second lead wire interfaces; and wherein said single male connector is a single-use connector whereby said single male connector is not readily reusable to effectively discourage re-use of the percutaneous and transcutaneous electrodes.

5. The apparatus of claim 4, wherein said single male connector and said single mating female receptacle are keyed to ensure proper orientation and electrical coupling of said first and second lead wires with the respective first and second lead wire interfaces of said pulse generator.

6. The apparatus of claim 4 wherein said single use connector includes a fuse adapted to burn out after a preselected time period.

7. The apparatus of claim 4 wherein said single use connector includes an EPROM programmed to prevent electrical connection of said first and second lead wires with said first and second lead wire interfaces.

8. The apparatus of claim 4 wherein said single use connector includes a fuse and an EPROM programmed to burn out said fuse after a predetermined time period.

9. The apparatus of claim 4 wherein said single use connector includes a fuse and an EPROM programmed to generate a current spike to burn out said fuse after a predetermined time period.

10. An electro-nerve stimulation apparatus, comprising:
a pulse generator for generating electrical pulses, said pulse generator having a first lead wire interface and a second lead wire interface;
a percutaneous needle electrode; and
a lead wire set removably connectable to the pulse generator and comprising:
a first electrically conductive, insulated lead wire having first and second ends, said first end of said first lead wire comprising a first connector for electrically coupling with said first lead wire interface of said pulse generator, said second end of said first lead wire operably comprising an electrically conductive transcutaneous electrode for delivering electrical pulses generated by the pulse generator to a patient's skin;
a second electrically conductive, insulated lead wire having first and second ends, said first end of said second lead wire comprising a second connector for electrically coupling with said second lead wire interface of said pulse generator, said second end of said second lead wire comprising an electrically conductive and mechanically suspendable attachment member for being suspended by and electrically connecting with said percutaneous needle electrode; and
a single-use mechanism comprising a part of said lead wire set to effectively discourage re-use thereof;
wherein said attachment member includes a clip having an electrically conductive bridge member movable between a first open position and a second closed position;
wherein a terminal end of said percutaneous needle electrode is secured to said electrically conductive bridge member;
wherein said clip is a single-use clip; and
wherein said bridge member fails after a predetermined time period of current pulses traverse therethrough.

11. An electro-nerve stimulation apparatus, comprising:
a pulse generator for generating electrical pulses, said pulse generator having a first lead wire interface and a second lead wire interface;
a percutaneous needle electrode; and
a lead wire set removably connectable to the pulse generator and comprising:
a first electrically conductive, insulated lead wire having first and second ends, said first end of said first lead wire comprising a first connector for electrically coupling with said first lead wire interface of said pulse generator, said second end of said first lead wire operably comprising an electrically conductive transcutaneous electrode for delivering electrical pulses generated by the pulse generator to a patient's skin;
a second electrically conductive, insulated lead wire having first and second ends, said first end of said second lead wire comprising a second connector for electrically coupling with said second lead wire interface of said pulse generator, said second end of said second lead wire comprising an electrically conductive and mechanically suspendable attachment member for being suspended by and electrically connecting with said percutaneous needle electrode; and
a single-use mechanism comprising a part of said lead wire set to effectively discourage re-use thereof;
wherein said attachment member includes a clip having an electrically conductive bridge member movable between a first open position and a second closed position;
wherein a terminal end of said percutaneous needle electrode is secured to said electrically conductive bridge member;
wherein said clip is a single-use clip; and
wherein said bridge member welds to said terminal end of said percutaneous needle electrode after a predetermined time period of current pulses traverse therethrough.

12. An electro-nerve stimulation apparatus, comprising:
a pulse generator for generating electrical pulses, said pulse generator having a first lead wire interface and a second lead wire interface;
a single male connector; and
a lead wire set removably connectable to the pulse generator and comprising;
a first electrically conductive, insulated lead wire having first and second ends, said first end of said first lead wire comprising a first connector for electrically coupling with said first lead wire interface of said pulse generator, said second end of said first lead wire operably comprising an electrically conductive transcutaneous electrode for delivering electrical pulses generated by the pulse generator to a patient's skin;
a second electrically conductive, insulated lead wire having first and second ends, said first end of said second lead wire comprising a second connector for electrically coupling with said second lead wire interface of said pulse generator, said second end of said second lead wire comprising an electrically conductive and mechanically suspendable attachment member for being suspended by and electrically connecting with a percutaneous needle electrode; and
a single-use mechanism comprising a part of said lead wire set to effectively discourage re-use thereof;

wherein said attachment member includes a clip having an electrically conductive bridge member movable between a first open position and a second closed position;
wherein the single male conductor comprises said first and second connectors fixedly secured to said first ends of said first and second lead wires;
wherein said pulse generator includes a single mating female receptacle for electrically coupling said first and second lead wires with said first and second lead wire interfaces; and
wherein said single male connector and said mating single female receptacle are keyed to ensure proper orientation and electrical coupling of said first and second lead wires only with the respective first and second lead wire interfaces of said pulse generator.

13. The apparatus of claim 12, wherein said single male connector is a single-use connector whereby said single male connector is not readily reusable.

14. The apparatus of claim 13 wherein said single use connector includes a fuse adapted to burn out after a preselected time period.

15. The apparatus of claim 13 wherein said single use connector includes an EPROM programmed to prevent electrical connection of said first and second lead wires with said first and second lead wire interfaces.

16. The apparatus of claim 13 wherein said single use connector includes a fuse and an EPROM programmed to burn out said fuse after a predetermined time period.

17. The apparatus of claim 13 wherein said single use connector includes a fuse and an EPROM programmed to generate a current spike to burn out said fuse after a predetermined time period.

18. A method for electro-nerve stimulation, comprising the steps of:
providing a pulse generator for generating electrical pulses, said pulse generator having a first lead wire interface and a second lead wire interface;
providing a removably connectable lead wire set for the pulse generator; providing the lead wire set with a first electrically conductive, insulated lead wire having first and second ends, said first end of said first lead wire comprising a connector for electrically coupling with said first lead wire interface of said pulse generator, said second end of said first lead wire operably comprising an electrically conductive transcutaneous electrode for delivering electrical pulses generated by said pulse generator to a patient's skin;
providing an electrically conductive percutaneous needle electrode, said electrically conductive percutaneous needle electrode having one end insertable into a patient's body in proximity to a preselected internal stimulation site to receive electrical pulses from said transcutaneous electrode;
providing the lead wire set with a second electrically conductive, insulated lead wire having first and second ends, said first end of said second lead wire comprising a connector for electrically coupling with said second lead wire interface of said pulse generator, said second end of said second lead wire comprising an electrically conductive and mechanically suspendable attachment member;
providing the lead wire set with a single-use mechanism to effectively discourage re-use thereof;
penetrating said patient's skin with said one end of said percutaneous needle electrode and advancing said one end into proximity with said preselected internal stimulation site;
electrically connecting a terminal end of said percutaneous needle electrode to said attachment member;
adhering said transcutaneous electrode onto said patient's skin distal to said preselected internal stimulation site;
electrically coupling said first and second lead wires with said respective first and second lead wire interfaces of said pulse generator; and
activating said pulse generator to generate electrical pulses that traverse the preselected internal stimulation site between said transcutaneous electrode and said percutaneous needle electrode;
wherein said electrically conductive transcutaneous electrode includes adhesive on a face thereof for removably securing said electrode onto said skin of said patient; and
wherein said adhesive on said face of said transcutaneous electrode is a single-use adhesive such that upon removal of said transcutaneous electrode from said patient's skin said adhesive will not readily re-adhere to said patient's skin.

19. A method for electro-nerve stimulation, comprising the steps of:
providing a pulse generator for generating electrical pulses, said pulse generator having a first lead wire interface and a second lead wire interface;
providing a removably connectable lead wire set for the pulse generator;
providing the lead wire set with a first electrically conductive, insulated lead wire having first and second ends, said first end of said first lead wire comprising a connector for electrically coupling with said first lead wire interface of said pulse generator, said second end of said first lead wire operably comprising an electrically conductive transcutaneous electrode for delivering electrical pulses generated by said pulse generator to a patient's skin;
providing an electrically conductive percutaneous needle electrode, said electrically conductive percutaneous needle electrode having one end insertable into a patient's body in proximity to a preselected internal stimulation site to receive electrical pulses from said transcutaneous electrode;
providing the lead wire set with a second electrically conductive, insulated lead wire having first and second ends, said first end of said second lead wire comprising a connector for electrically coupling with said second lead wire interface of said pulse generator, said second end of said second lead wire comprising an electrically conductive and mechanically suspendable attachment member;
providing the lead wire set with a single-use mechanism to effectively discourage re-use thereof;
penetrating said patient's skin with said one end of said percutaneous needle electrode and advancing said one end into proximity with said preselected internal stimulation site;
electrically connecting a terminal end of said percutaneous needle electrode to said attachment member;
adhering said transcutaneous electrode onto said patient's skin distal to said preselected internal stimulation site;
electrically coupling said first and second lead wires with said respective first and second lead wire interfaces of said pulse generator; and
activating said pulse generator to generate electrical pulses that traverse the preselected internal stimulation site between said transcutaneous electrode and said percutaneous needle electrode;

wherein said attachment member includes an electrically conductive tape member having an adhesive portion; and wherein said step of connecting said terminal end of said percutaneous needle electrode to said attachment member includes the step of fixedly adhering said adhesive portion of said electrically conductive tape member to said terminal end, whereby said percutaneous needle electrode is not readily removable therefrom without damaging said tape member;

further including the step of testing proper placement of said one end of said percutaneous needle electrode in proximity to said preselected internal stimulation site prior to fixedly adhering said terminal end of said percutaneous needle electrode to said adhesive portion of said electrically conductive tape member by contacting said other end of said percutaneous needle with a non-adhesive electrically conductive portion of said electrically conductive tape member.

20. A method for electro-nerve stimulation, comprising the steps of:

providing a pulse generator for generating electrical pulses, said pulse generator having a first lead wire interface and a second lead wire interface;

providing a first electrically conductive, insulated lead wire having first and second ends, said first end of said first lead wire fixedly secured to a connector for electrically coupling with said first lead wire interface of said pulse generator, said second end of said first lead wire operably secured to an electrically conductive transcutaneous electrode for delivering electrical pulses generated by said pulse generator to a patient's skin;

providing an electrically conductive percutaneous needle electrode, said electrically conductive percutaneous needle electrode having one end insertable into a patient's body in proximity to a preselected internal stimulation site to receive electrical pulses from said transcutaneous electrode;

providing a second electrically conductive, insulated lead wire having first and second ends, said first end of said second lead wire fixedly secured to a connector for electrically coupling with said second lead wire interface of said pulse generator, said second end of said second lead wire fixedly secured to an electrically conductive adaptor;

penetrating said patient's skin with said one end of said percutaneous needle electrode and advancing said one end into proximity with said preselected internal stimulation site;

electrically connecting a terminal end of said percutaneous needle electrode to said electrically conductive single-use adaptor;

adhering said transcutaneous electrode onto said patient's skin distal to said preselected internal stimulation site;

electrically coupling said first and second lead wires with said respective first and second lead wire interfaces of said pulse generator; and activating said pulse generator to generate electrical pulses that traverse the preselected internal stimulation site between said transcutaneous electrode and said percutaneous needle electrode;

wherein said first and second connectors fixedly secured to said first ends of said first and second lead wires comprise a single male connector;

wherein said pulse generator includes a single mating female receptacle for electrically coupling said first and second lead wires with said first and second lead wire interfaces; and wherein said single male connector is a single-use connector whereby said single male connector is not readily reusable to effectively discourage re-use of said percutaneous and transcutaneous electrodes.

21. The method of claim 20, wherein said single male connector and said mating single female receptacle are keyed to ensure proper orientation and electrical coupling of said first and second lead wires with the respective first and second lead wire interfaces of said pulse generator.

22. The method of claim 20 wherein said single use connector includes a fuse adapted to burn out after a preselected time period.

23. The method of claim 20 wherein said single use connector includes an EPROM programmed to prevent electrical connection of said first and second lead wires with said first and second lead wire interfaces.

24. The method of claim 20 wherein said single use connector includes a fuse and an EPROM programmed to burn out said fuse after a predetermined time period.

25. The method of claim 20 wherein said single use connector includes a fuse and an EPROM programmed to generate a current spike to burn out said fuse after a predetermined time period.

26. A method for electro-nerve stimulation, comprising the steps of:

providing a pulse generator for generating electrical pulses, said pulse generator having a first lead wire interface and a second lead wire interface;

providing a removably connectable lead wire set for the pulse generator;

providing the lead wire set with a first electrically conductive, insulated lead wire having first and second ends, said first end of said first lead wire comprising a connector for electrically coupling with said first lead wire interface of said pulse generator, said second end of said first lead wire operably comprising an electrically conductive transcutaneous electrode for delivering electrical pulses generated by said pulse generator to a patient's skin;

providing an electrically conductive percutaneous needle electrode, said electrically conductive percutaneous needle electrode having one end insertable into a patient's body in proximity to a preselected internal stimulation site to receive electrical pulses from said transcutaneous electrode;

providing the lead wire set with a second electrically conductive, insulated lead wire having first and second ends, said first end of said second lead wire comprising a connector for electrically coupling with said second lead wire interface of said pulse generator, said second end of said second lead wire comprising an electrically conductive and mechanically suspendable attachment member;

providing the lead wire set with a single-use mechanism to effectively discourage re-use thereof;

penetrating said patient's skin with said one end of said percutaneous needle electrode and advancing said one end into proximity with said preselected internal stimulation site;

electrically connecting a terminal end of said percutaneous needle electrode to said attachment member;

adhering said transcutaneous electrode onto said patient's skin distal to said preselected internal stimulation site;

electrically coupling said first and second lead wires with said respective first and second lead wire interfaces of said pulse generator; and activating said pulse generator to generate electrical pulses that traverse the preselected internal stimulation site between said transcutaneous electrode and said percutaneous needle electrode;

wherein said attachment member includes a clip having an electrically conductive bridge member movable between a first open position and a second closed position;

wherein said step of connecting said terminal end of said percutaneous needle electrode to said attachment member includes the step of connecting said terminal end of said percutaneous needle electrode to said electrically conductive bridge member;

wherein said clip is a single-use clip; and wherein said bridge member fails after a predetermined time period of current pulses traverse therethrough.

27. A method for electro-nerve stimulation, comprising the steps of:

providing a pulse generator for generating electrical pulses, said pulse generator having a first lead wire interface and a second lead wire interface;

providing a removably connectable lead wire set for the pulse generator;

providing the lead wire set with a first electrically conductive, insulated lead wire having first and second ends, said first end of said first lead wire comprising a connector for electrically coupling with said first lead wire interface of said pulse generator, said second end of said first lead wire operably comprising an electrically conductive transcutaneous electrode for delivering electrical pulses generated by said pulse generator to a patient's skin;

providing an electrically conductive percutaneous needle electrode, said electrically conductive percutaneous needle electrode having one end insertable into a patient's body in proximity to a preselected internal stimulation site to receive electrical pulses from said transcutaneous electrode;

providing the lead wire set with a second electrically conductive, insulated lead wire having first and second ends, said first end of said second lead wire comprising a connector for electrically coupling with said second lead wire interface of said pulse generator, said second end of said second lead wire comprising an electrically conductive and mechanically suspendable attachment member;

providing the lead wire set with a single-use mechanism to effectively discourage re-use thereof;

penetrating said patient's skin with said one end of said percutaneous needle electrode and advancing said one end into proximity with said preselected internal stimulation site;

electrically connecting a terminal end of said percutaneous needle electrode to said attachment member;

adhering said transcutaneous electrode onto said patient's skin distal to said preselected internal stimulation site;

electrically coupling said first and second lead wires with said respective first and second lead wire interfaces of said pulse generator; and activating said pulse generator to generate electrical pulses that traverse the preselected internal stimulation site between said transcutaneous electrode and said percutaneous needle electrode;

wherein said attachment member includes a clip having an electrically conductive bridge member movable between a first open position and a second closed position;

wherein said step of connecting said terminal end of said percutaneous needle electrode to said attachment member includes the step of connecting said terminal end of said percutaneous needle electrode to said electrically conductive bridge member;

wherein said clip is a single-use clip; and wherein said bridge member welds to said terminal end of said percutaneous needle electrode after a predetermined time period of current pulses traverse therethrough.

28. A method for electro-nerve stimulation, comprising the steps of:

providing a pulse generator for generating electrical pulses, said pulse generator having a first lead wire interface and a second lead wire interface;

providing a removably connectable lead wire set for the pulse generator;

providing the lead wire set with a first electrically conductive, insulated lead wire having first and second ends, said first end of said first lead wire comprising a connector for electrically coupling with said first lead wire interface of said pulse generator, said second end of said first lead wire operably comprising an electrically conductive transcutaneous electrode for delivering electrical pulses generated by said pulse generator to a patient's skin;

providing an electrically conductive percutaneous needle electrode, said electrically conductive percutaneous needle electrode having one end insertable into a patient's body in proximity to a preselected internal stimulation site to receive electrical pulses from said transcutaneous electrode;

providing the lead wire set with a second electrically conductive, insulated lead wire having first and second ends, said first end of said second lead wire comprising a connector for electrically coupling with said second lead wire interface of said pulse generator, said second end of said second lead wire comprising an electrically conductive and mechanically suspendable attachment member;

providing the lead wire set with a single-use mechanism to effectively discourage re-use thereof;

penetrating said patient's skin with said one end of said percutaneous needle electrode and advancing said one end into proximity with said preselected internal stimulation site;

electrically connecting a terminal end of said percutaneous needle electrode to said attachment member;

adhering said transcutaneous electrode onto said patient's skin distal to said preselected internal stimulation site;

electrically coupling said first and second lead wires with said respective first and second lead wire interfaces of said pulse generator; and activating said pulse generator to generate electrical pulses that traverse the preselected internal stimulation site between said transcutaneous electrode and said percutaneous needle electrode;

wherein said attachment member includes a clip having an electrically conductive bridge member movable between a first open position and a second closed position; and wherein said first and second connectors fixedly secured to said first ends of said first and second lead wires comprise a single male connector and wherein said pulse generator includes a single mating female receptacle for electrically coupling said first and second lead wires with said first and second lead wire interfaces, and further wherein said single male connector and said mating single female receptacle are keyed to ensure proper orientation and electrical coupling of said first and second lead wires only with the respective first and second lead wire interfaces of said pulse generator.

29. The method of claim 28, wherein said single male connector is a single-use connector whereby said single male connector is not readily reusable.

30. The method of claim 29 wherein said single use connector includes a fuse adapted to burn out after a preselected time period.

31. The method of claim 29 wherein said single use connector includes an EPROM programmed to prevent electrical connection of said first and second lead wires with said first and second lead wire interfaces.

32. The method of claim 29 wherein said single use connector includes a fuse and an EPROM programmed to burn out said fuse after a predetermined time period.

* * * * *